(12) United States Patent
Zhong et al.

(10) Patent No.: US 9,815,029 B2
(45) Date of Patent: Nov. 14, 2017

(54) METHOD FOR PREPARING ANTIBACTERIAL AND DUST-REMOVAL MEMBRANE

(71) Applicant: NANJING TECH UNIVERSITY, Nanjing (CN)

(72) Inventors: Zhaoxiang Zhong, Nanjing (CN); Xibo Wu, Nanjing (CN); Zhong Yao, Nanjing (CN)

(73) Assignee: Nanjing Tech University, Nanjing (CN)

( * ) Notice: Subject to any disclaimer, the term of this patent is extended or adjusted under 35 U.S.C. 154(b) by 109 days.

(21) Appl. No.: 15/028,854

(22) PCT Filed: Jul. 20, 2015

(86) PCT No.: PCT/CN2015/084475
§ 371 (c)(1),
(2) Date: Apr. 12, 2016

(87) PCT Pub. No.: WO2016/173126
PCT Pub. Date: Nov. 3, 2016

(65) Prior Publication Data
US 2017/0259213 A1  Sep. 14, 2017

(30) Foreign Application Priority Data
Apr. 28, 2015  (CN) .......................... 2015 1 0210127

(51) Int. Cl.
*B01D 67/00* (2006.01)
*B01D 53/22* (2006.01)
(Continued)

(52) U.S. Cl.
CPC ............ *B01D 67/0051* (2013.01); *A61L 9/16* (2013.01); *B01D 53/228* (2013.01);
(Continued)

(58) Field of Classification Search
CPC ........... B01D 67/0051; B01D 67/0072; B01D 67/0083; B01D 67/009; B01D 67/02;
(Continued)

(56) References Cited

U.S. PATENT DOCUMENTS

| 6,299,778 | B1 * | 10/2001 | Penth | ................. | B01D 46/0056 204/554 |
| 6,309,545 | B1 * | 10/2001 | Penth | ................. | B01D 46/0056 210/490 |

(Continued)

FOREIGN PATENT DOCUMENTS

| CN | 1272391 A | 11/2000 |
| CN | 101265123 | 12/2010 |

(Continued)

OTHER PUBLICATIONS

Lifeng Zhang, Jie Luo, Todd Menkhaus, Hemanthram Varadaraju, Yuyu Sun, Hao Fong. Antimicrobial nano-fibrous membranes developed from electrospun polyacrylonitrile nanofibers. J. Membr. Sci. 2011, 369, 499-505.

*Primary Examiner* — Duy Deo
(74) *Attorney, Agent, or Firm* — Treasure IP Group, LLC

(57) ABSTRACT

This invention discloses a method for preparing an antibacterial and dust-removal membrane. The method comprises the following steps: depositing a layer of nano-ZnO on the immersed membrane surface as the seed crystal with the atomic layer deposition instrument (ALD instrument); vertically immersing the membrane covered with nano-ZnO layer in a hydrothermal reactor filled with crystal growth solution, heating it for a period of time, taking the membrane out and cooling it to the room temperate, and removing it from the substrate; finally, heating this membrane in a drier, and purging it with nitrogen to remove the paraffin within (Continued)

the membrane pore to obtain the porous membrane with nano-ZnO arrays growing on the surface.

7 Claims, 3 Drawing Sheets

(51) Int. Cl.
    *B01D 71/02*     (2006.01)
    *B01D 69/02*     (2006.01)
    *C23C 16/455*     (2006.01)
    *C23C 16/56*     (2006.01)
    *A61L 9/16*     (2006.01)

(52) U.S. Cl.
    CPC ....... *B01D 67/009* (2013.01); *B01D 67/0072* (2013.01); *B01D 67/0083* (2013.01); *B01D 69/02* (2013.01); *B01D 71/025* (2013.01); *C23C 16/45555* (2013.01); *C23C 16/56* (2013.01); *A61L 2209/14* (2013.01); *B01D 2053/221* (2013.01); *B01D 2323/286* (2013.01); *B01D 2325/48* (2013.01)

(58) Field of Classification Search
    CPC ... B01D 71/025; A61L 9/16; C23C 16/45555; C23C 16/56
    See application file for complete search history.

(56) References Cited

U.S. PATENT DOCUMENTS

| | | | |
|---|---|---|---|
| 6,383,386 B1 | 5/2002 | Hying et al. | |
| 6,472,016 B1 * | 10/2002 | Soria | B01D 53/228 427/245 |
| 2016/0303148 A1 * | 10/2016 | Kozono | A61K 9/0014 |
| 2017/0156356 A1 * | 6/2017 | Omenetto | A23B 7/16 |

FOREIGN PATENT DOCUMENTS

| | | |
|---|---|---|
| CN | 101342467 | 11/2011 |
| CN | 103537197 | 1/2014 |

\* cited by examiner

METHOD FOR PREPARING ANTIBACTERIAL AND DUST-REMOVAL MEMBRANE

CROSS REFERENCE TO RELATED APPLICATION

This application is a National Phase application of, and claims priority to, PCT Application No. PCT/CN 2015/084475, filed on Jul. 20, 2015 entitled "Method for Preparing Antibacterial and Dust-removal Membrane", which claims priority to Chinese Application No. 201510210127.0, filed on Apr. 28, 2015. Both the PCT Application and Chinese Application are incorporated herein by reference in their entireties.

TECHNICAL FIELD

The present invention belongs to the field of preparation and modification of membrane and, more particularly, relates to a modification method for growing crystal on the surface of porous membrane and keeping the pores clean.

BACKGROUND ART

Air pollution, one of the environmental problems, has seriously harmed our life, as well as industrial and agricultural production. More attentions have been given to the treatment of air pollution. No matter in the industry or society, it is urgent to develop new air purification methods, and reduce the emission of harmful gas.

Currently, the air is mainly purified through ozone-catalytic and photocatalytic chemical decomposition, activated carbon adsorption and filtration. While generating a large amount of high concentration ozone to kill some viruses and bacteria, an ozone generator may kill the human leukocytes and cause canceration; the photocatalyst may take effect relying on the ultraviolet irradiation, and may harm human body and plastics; the activated carbon adsorption shall be replaced after reaching the saturated state one month later; the saturated one cannot kill any bacteria, and may cause bacterial reproduction.

The technology of inorganic membrane separation and purification is rapidly developed in recent years, and may be applied for filtering the bacteria, particulate matters and other pollutants in fluid and gas. Anodic aluminum oxide membrane is a kind of nano inorganic membrane for filtering with highly regular pores, and can realize the filtration through pores with the diameter of several to hundreds of nanometers, so it is an ideal air filtering material. However, the bacteria and pollutants rejected and held back during filtering may attach on the membrane surface or in the pores with a concentration higher than that in the water and air, making it more easy to reproduce bacteria; the bacterial reproduction on membrane surface or in pore will block the pore, increase the filtering resistance, and decrease the filtration flux significantly, which is one of major reasons for membrane pollution and blockage.

The nano-ZnO is excellent in antibacterial action and bacteriostasis; similar to the photocatalytic mechanism, the bactericidal mechanism is that the antibacterial action is realized through damaging the microorganism with reactive oxygen generated by nano ZnO. One layer of ZnO membrane which is adhered to the surface of sterile membrane will reduce the adhesion and reproduction of rejected bacteria on membrane surface, improving the service life of inorganic membrane, and reducing the pollution and blockage of membrane.

SUMMARY OF THE INVENTION

The present invention provides a method for preparing an antibacterial and dust-removal membrane to combine the AAO membrane and nano-ZnO for a better antibacterial and bactericidal action than the single AAO membrane for the convenience of practical application, with its hardness improved.

The present invention is realized through the following technical scheme.

A method for preparing an antibacterial and dust-removal membrane, the method comprising the following steps:
(1) Pretreatment: washing an AAO porous membrane with ethanol solution, and melting the paraffin for future use;
(2) Pore blockage: adhering the pretreated AAO porous membrane on the substrate horizontally and closely, clamping on a glass slide with a clamping slot, immersing the glass slide in the paraffin solution and vibrating, taking the glass slide out after a period of time, cooling it to the room temperature with the surface exposed to the paraffin upward, using a hot smooth iron sheet to remove most of the paraffin on the surface of porous membrane, and removing the residual solid paraffin on the surface through plasma etching;
(3) Crystal seeding: placing the AAO membrane in the reaction chamber of the ALD instrument after it is ultrasonically cleaned with acetone, ethanol and deionized water, using the diethylzinc and deionized water as the precursor source respectively to provide zinc and oxygen required for the growth of ZnO, and using high purity nitrogen as the carrier and purging gas, starting deposition after the vacuum degree reaches to 15~20 Pa, keeping the deposition cycle for hundreds of times;
(4) Crystal growth: preparing the mixed solution of hexamethylene tetramine and zinc nitrate of certain concentration in proportion as the growth solution, pouring the solution in a hydrothermal reactor, vertically placing the substrate with the AAO porous membrane covered with ZnO layer in the hydrothermal reactor, placing the hydrothermal reactor in a drier to treat for a period of time, cooling naturally, taking the membrane out, washing it with deionized water, and drying it to obtain the porous membrane with nano-ZnO arrays on the surface;
(5) Pore cleaning: removing the porous membrane obtained in Step (4) from the substrate, horizontally placing the membrane in a drier and ensuring that the side is covered with nano-ZnO arrays upwards, heating for a period of time, purging the membrane with nitrogen, cooling and obtaining a porous membrane with nano-ZnO arrays growing on the surface and uniform permeable pores.

In Step (1), the pore diameter of the said AAO porous membrane is 0.1-10 μm; and the mass concentration of the said ethanol solution is 80~95%.

In Step (2), the immersion temperature is 60~90° C., and the immersion time is 3~5 h; and the temperature of the said hot iron sheet is 60~70° C. The gas mixture of $CH_4$, $H_2$ and Ar is adopted for said plasma etching, in which the molar ratio is 1:7:5; the flow of the said gas is 26~78 sccm; the bias power is 80~90 W; the radio-frequency power is 250~300 W; the etching speed is 10~25 nm/main, and the etching time is 1~2 h.

In Step (3), the pulse time and washing time of the said diethylzinc are 0.1~0.2 s and 3~4 s respectively; the pulse time and washing time of the said deionized water are 0.1~0.2 s and 4~5 s respectively; The flows of carrier gas of diethylzinc and deionized water respectively are 100~150 sccm and 150~200 sccm; the temperature of substrate is 200~280° C.; And the number of time for growing is 100~200 cycles.

In Step (4), the concentrations of hexamethylene tetramine and zinc nitrate in said mixed solution are both 0.003~0.1 mol/L; the molar ratio of those substances in the solution is 1:1; and the addition dose of the said mixed solution is 100~500 ml.

In Step (5), the temperature of the said drier in is 60~90° C.; the flow rate of nitrogen is 0.4~0.5 m/s, and the pressure is 0.5~0.6 MPa.

The Beneficial Effects of the Present Invention

The filtering membrane prepared through the method in the present invention is large in air flow capacity, good in mechanical strength, and convenient for practical application;

The method of seeding and growth in solution used in the present invention can realize the oriented growth of ZnO membrane. It is featured by lower energy consumption, higher output, simple instrument and equipment, easier to operate and possible of scale production compared with the results of traditional method;

This method enables the nano-ZnO arrays closely adhere on the surface of porous membrane and make them difficult to fall off, offering a long service life to the membrane;

In the present invention, the surface of porous membrane may be generated with nano-ZnO of the same thickness, which is easy to be controlled;

Through gas antibacterial experiment, the antibacterial performance of the membrane reaches to 99.99%; the surface filtering is adopted without affecting the air permeability; compared with other air filtering material, the membrane is stable, easy to clean, and long in service life.

EMBODIMENTS

Figure 1:
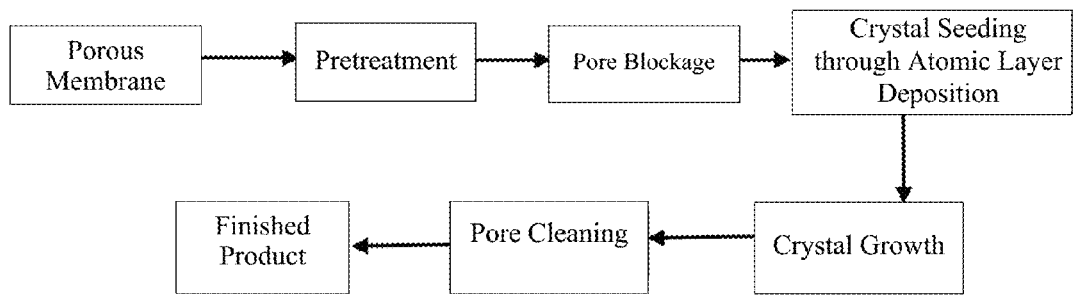
FIG. 1 is the process flow for preparing an antibacterial and dust-removal membrane.

The present invention is illustrated in combination with the following embodiments, which are only for illustration, not for limiting the scope of implementation.

Embodiment 1

(1) Pretreatment: washing the 0.1 μm AAO porous membrane by 80% (w/v) ethanol, and melting the paraffin for future use;

(2) Pore blockage: adhering the pretreated AAO porous membrane on the substrate horizontally and closely, clamping on the glass slide with a clamping slot, and immersing the glass slide in the paraffin solution and vibrating, taking it out after immersing at a temperature of 70° C. for 3 h, cooling it to the room temperature with the surface exposed to paraffin upward, using a 60° C. hot smooth iron sheet to remove most of paraffin on the surface of porous membrane; using the gas mixture of $CH_4$, $H_2$ and Ar (with the molar ratio of 1:7:5) as etching gas, and removing the residual solid paraffin on the surface through plasma etching, in which the flow of gas used is 26 sccm; the bias power and radio-frequency power respectively are 80 W and 250 W; the etching rate and time are 10 nm/min and 120 min respectively;

(3) Seeding: placing the AAO membrane in the reaction chamber of an ALD instrument after it is ultrasonically cleaned with acetone, ethanol and deionized water, using the diethylzinc and deionized water as the precursor source respectively to provide zinc and oxygen required for the growth of ZnO, and using the high purity nitrogen as the carrier and purging gas, in which the pulse time and washing time of diethylzinc are 0.1 s and 3 s respectively; the pulse time and washing time of the said deionized water are 0.1 and 4 s respectively; the flows of carrier gas of diethylzinc and deionized water are 100 sccm and 150 sccm respectively; the temperature of substrate is 200° C.; the number of time for growing is 100 cycles; and the deposition is started at the vacuum degree of 20 Pa;

(4) Crystal growth: preparing the mixed solution of hexamethylene tetramine (with the concentration of 0.003 mol/L) and zinc nitrate (with the concentration of 0.003 mol/L) as the growth solution, in which the molar ratio of those substances is 1:1; pouring 100 ml mixed solution in a hydrothermal reactor, vertically placing the substrate with the AAO porous membrane covered with ZnO layer in the hydrothermal reactor, placing the hydrothermal reactor in the 80° C. drier to treat for 4 h, cooling it naturally, taking the membrane out, washing it with deionized water, and making it dry;

(5) Pore cleaning: removing the porous membrane obtained in Step (4) from the substrate, horizontally placing the membrane in a 60° C. drier and ensuring that the side is covered with nano-ZnO arrays upwards, purging the membrane with nitrogen with a flow rate of 0.4 m/s and pressure of 0.5 MPa, cooling it and obtaining the porous membrane with nano-ZnO arrays growing on the surface and uniform permeable pores.

Figure 2:
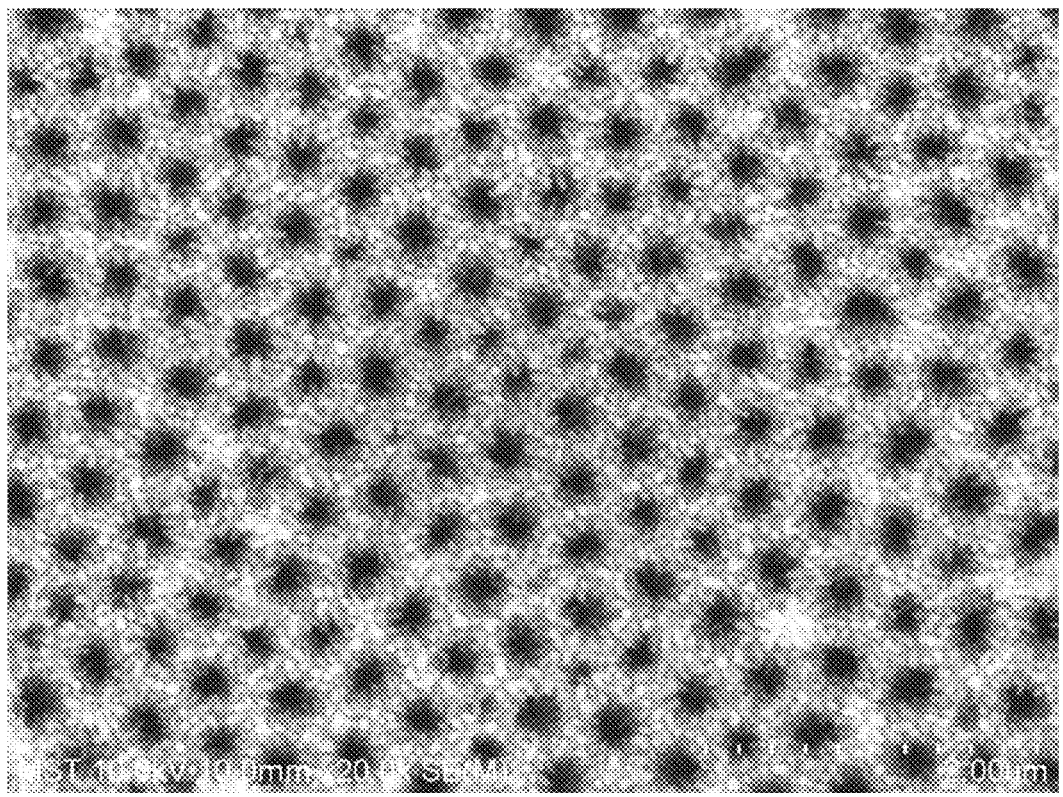
FIGS. 2, 3 and 4 are the scanning electron microscopes of antibacterial and dust-removal membrane under different preparation conditions measured by scanning electron microscope S-4800.

The air purification membrane prepared in this Embodiment is measured by scanning electron microscope S-4800, as shown in FIG. 2. The surface of AAO membrane is formed with tapered granular ZnO crystal, and the air purification membrane is 0.2 mm thick with a pore size of 0.2~0.3 um. According to the antibacterial experiment [J. Membr. Sci. 2011, 369, 499], the antimicrobial effect is 96.49%, especially for positive bacteria and non-spore bacteria.

Embodiment 2

(1) Pretreatment: washing an 1 μm AAO porous membrane by 90% (w/v) ethanol, and melting the paraffin for future use;

(2) Pore blockage: adhering the pretreated AAO porous membrane on the substrate horizontally and closely, clamping on the glass slide with a clamping slot, and immersing the glass slide in the paraffin solution and vibrating, taking it out after immersing at a temperature of 60° C. for 5 h, cooling it to the room temperature with the surface exposed to paraffin upward, using a 65° C. hot smooth iron sheet to remove most of paraffin on the surface of porous membrane; using the gas mixture of $CH_4$, $H_2$ and Ar (with the molar ratio of 1:7:5) as etching gas, and removing the residual solid paraffin on the surface through plasma etching, in which the flow of gas used is 39 sccm; the bias power and radio-frequency power respectively are 90 W and 300 W; the etching rate and time are 18 nm/min and 90 min respectively;

(3) Seeding: placing the AAO membrane in the reaction chamber of an ALD instrument after it is ultrasonically cleaned with acetone, ethanol and deionized water, using the diethylzinc and deionized water as the precursor source respectively to provide zinc and oxygen required for the growth of ZnO, and using the high purity nitrogen as the carrier and purging gas, in which the pulse time and washing time of diethylzinc are 0.2 s and 4 s respectively; the pulse time and washing time of the said deionized water are 0.2 and 5 s respectively; the flows of carrier gas of diethylzinc and deionized water are 120 sccm and 170 sccm respectively; the temperature of substrate is 240° C.; the number of time for growing is 150 cycles; and the deposition is started at the vacuum degree of 15 Pa;

(4) Crystal growth: preparing the mixed solution of hexamethylene tetramine (with the concentration of 0.025 mol/L) and zinc nitrate (with the concentration of 0.025 mol/L) as the growth solution, in which the molar ratio of those substances is 1:1; pouring 200 ml mixed solution in a hydrothermal reactor, vertically placing the substrate with the AAO porous membrane covered with ZnO layer in the hydrothermal reactor, placing the hydrothermal reactor in a 90° C. drier to treat for 3 h, cooling it naturally, taking the membrane out, washing it with deionized water, and making it dry;

(5) Pore cleaning: removing the porous membrane obtained in Step (4) from the substrate, horizontally placing the membrane in a drier and ensuring that the side is covered with nano-ZnO arrays upwards, purging the membrane with nitrogen with a flow rate of 0.5 m/s and pressure of 0.6 MPa, cooling it and obtaining the porous membrane with nano-ZnO arrays growing on the surface and uniform permeable pores.

Figure 3:
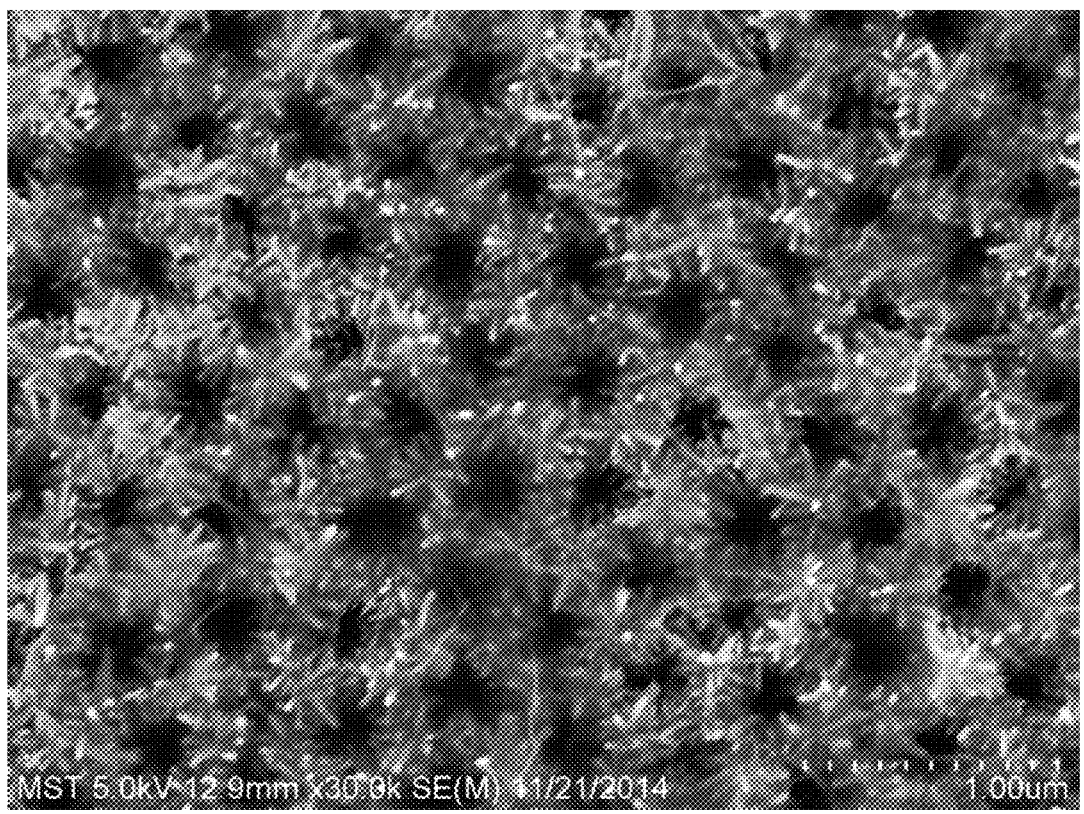

The air purification membrane prepared in this Embodiment is measured by scanning electron microscope S-4800, as shown in FIG. 3. The surface of AAO membrane is formed with filamentary ZnO crystal, and the air purification membrane is 0.4 mm thick with a pore size of 0.3~0.4 um. According to the antibacterial experiment [J. Membr. Sci. 2011, 369, 499], the antimicrobial effect is 95.8%, especially for positive bacteria and non-spore bacteria; the membrane is good in inhibition to negative bacteria and spore bacteria.

Embodiment 3

(1) Pretreatment: washing a 10 μm AAO porous membrane by 95% (w/v) ethanol, and melting the paraffin for future use;

(2) Pore blockage: adhering the pretreated AAO porous membrane on the substrate horizontally and closely, clamping on the glass slide with a clamping slot, and immersing the glass slide in the paraffin solution and vibrating, taking it out after immersing at a temperature of 90° C. for 5 h, cooling it to the room temperature with the surface exposed to paraffin upward, using a 70° C. hot smooth iron sheet to remove most of paraffin on the surface of porous membrane; using the gas mixture of $CH_4$, $H_2$ and Ar (with the molar ratio of 1:7:5) as etching gas, and removing the residual solid paraffin on the surface through plasma etching, in which the flow of gas used is 78 sccm; the bias power and radio-frequency power respectively are 90 W and 300 W; the etching rate and time are 25 nm/min and 60 min respectively;

(3) Seeding: placing the AAO membrane in the reaction chamber of an ALD instrument after it is ultrasonically cleaned with acetone, ethanol and deionized water, using the diethylzinc and deionized water as the precursor source respectively to provide zinc and oxygen required for the growth of ZnO, and using the high purity nitrogen as carrier gas and purging gas, in which the pulse time and washing time of diethylzinc are 0.2 s and 4 s respectively; the pulse time and washing time of the said deionized water are 0.2 and 5 s respectively; the flows of carrier gas of diethylzinc and deionized water are 150 sccm and 200 sccm respectively; the temperature of substrate is 280° C.; the number of time for growing is 200 cycles; and the deposition is started at the vacuum degree of 15 Pa;

(4) Crystal growth: preparing the mixed solution of hexamethylene tetramine (with the concentration of 0.1 mol/L) and zinc nitrate (with the concentration of 0.1 mol/L) as the growth solution, in which the molar ratio of those substances is 1:1; pouring 500 ml mixed solution in a hydrothermal reactor, vertically placing the substrate with the AAO porous membrane covered with ZnO layer in the hydrothermal reactor, placing the hydrothermal reactor in the 100° C. drier to treat for 4 h, cooling it naturally, taking the membrane out, washing it with deionized water, and making it dry;

(5) Pore cleaning: removing the porous membrane obtained in Step (4) from the substrate, horizontally placing the membrane in a drier and ensuring that the side is covered with nano-ZnO arrays upwards, purging the membrane with nitrogen with a flow rate of 0.5 m/s and pressure of 0.6 MPa, cooling and obtaining the porous membrane with nano-ZnO arrays growing on the surface and uniform permeable pores.

Figure 4:
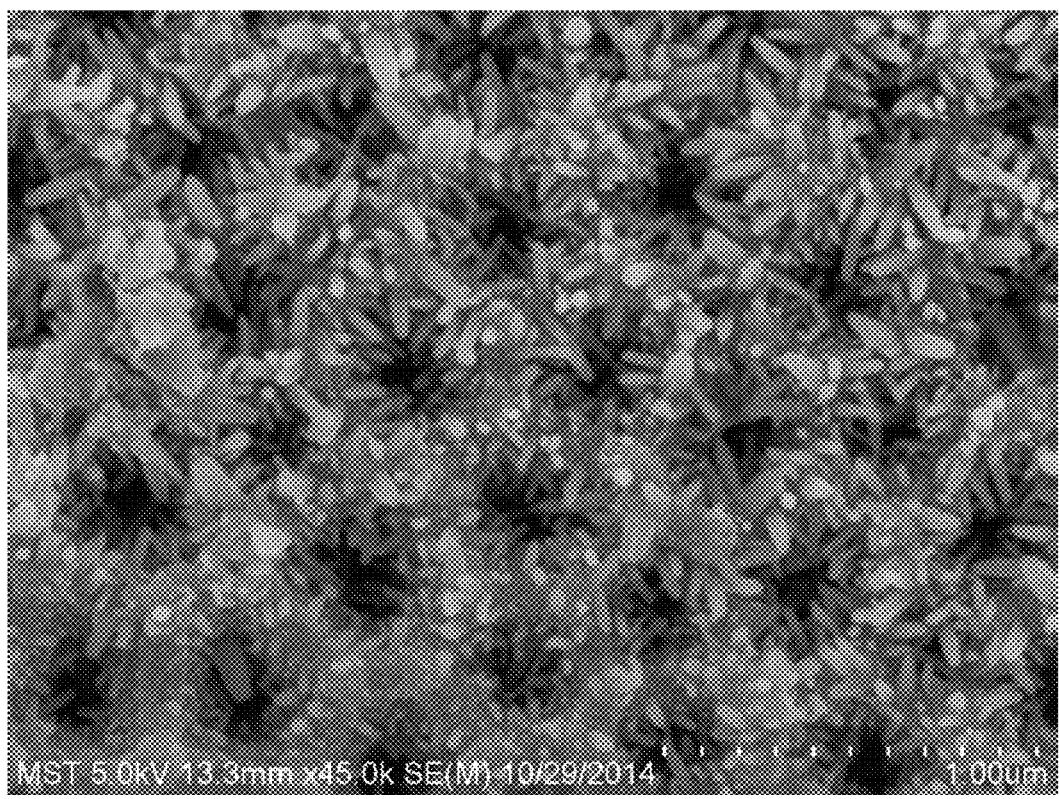

The air gas purification membrane prepared in this Embodiment is measured by scanning electron microscope S-4800, as shown in FIG. 4. The surface of AAO membrane is formed with even rodlike ZnO crystal, and the air purification membrane is 1 mm thick with a pore size of 0.1~0.25 um. According to the antibacterial experiment [J. Membr. Sci. 2011, 369, 499], the antimicrobial effect is 97.2%, capable of inhibiting the growth and permeation of various kinds of bacteria.

We claim:

1. A method for preparing an antibacterial and dust-removal membrane, comprising:

(1) performing a pretreatment step including: washing an AAO porous membrane with an ethanol solution, and melting a paraffin solution for future use;

(2) performing a pore blocking step including: adhering the pretreated AAO porous membrane on a substrate horizontally to prepare a sample, clamping the sample on a glass slide with a clamping slot, and immersing the glass slide having the sample in the paraffin solution and vibrating, taking the sample out after a period of time, cooling the sample to the room temperature with a surface exposed to the paraffin upward, using a hot smooth iron sheet to remove most of the paraffin on the surface of porous membrane, and removing the residual solid paraffin on the surface through plasma etching;

(3) performing a crystal seeding step including: placing the AAO membrane in the reaction chamber of ALD instrument after it is ultrasonically cleaned with acetone, ethanol and deionized water, using diethylzinc and deionized water as a precursor source respectively to provide zinc and oxygen required for the growth of ZnO, and using high purity nitrogen as a carrier and purging gas, starting deposition after it reaches to 15~20 Pa, and keeping the deposition for a few hundreds cycles;

(4) performing a crystal growth step including: preparing a mixed solution of hexamethylene tetramine and zinc nitrate of at certain concentration in proportion as a growth solution, pouring the growing solution into a hydrothermal reactor, vertically placing the substrate with the AAO porous membrane covered with ZnO layer in the hydrothermal reactor, placing the hydrothermal reactor in a drier for treatment for a period of time, cooling naturally, taking the membrane out, washing the membrane-with deionized water, and drying it to obtain the porous membrane with nano-ZnO arrays on the surface;

(5) performing a pore cleaning step including: removing the porous membrane obtained in Step (4) from the substrate, horizontally placing the membrane in a drier and ensuring that the side is covered with nano-ZnO arrays upwards, heating for a period of time, purging the membrane with nitrogen, cooling and obtaining a porous membrane with nano-ZnO arrays growing on the surface and having uniform permeable pores.

2. The method for preparing an antibacterial and dust-removal membrane of claim 1, wherein the pore diameter of AAO porous membrane in Step (1) is 0.1-10 μm; and the mass concentration of the ethanol solution is 80~95%.

3. The method for preparing an antibacterial and dust-removal membrane of claim 1, wherein the immersion temperature in Step (2) is 60~90° C., the immersion time is 3~5 h; and the temperature of said hot iron sheet is 60~70° C. and a gas mixture of $CH_4$, $H_2$ and Ar is adopted for said plasma etching, in which the molar ratio of the gases is 1:7:5; the flow of the gas is 26~78 sccm; a bias power is 80~90 W; a radio-frequency power is 250~300 W; etching speed is 10~25 nm/min, and etching time is 1~2 h.

4. The method for preparing an antibacterial and dust-removal membrane of claim 1, wherein pulse time and washing time of said diethylzinc in Step (3) are 0.1~0.2 s and 3~4 s respectively; pulse time and washing time of the deionized water are 0.1~0.2 s and 4~5 s respectively; the flows of carrier gas of diethylzinc and deionized water respectively are 100~150 sccm and 150~200 sccm; temperature of the substrate is 200~280° C.; and number of times for growing is 100~200 cycles.

5. The method for preparing an antibacterial and dust-removal membrane of claim 1, wherein the concentrations of hexamethylene tetramine and zinc nitrate in said mixed solution in Step (4) are both 0.003~0.1 mol/L; the molar ratio of hexamethylene tetramine and zinc nitrate in the solution is 1:1; and the addition dose of the mixed solution is 100~500 ml.

6. The method for preparing an antibacterial and dust-removal membrane of claim 1, wherein the temperature of said drier in Step (4) is 80~100° C., and the treatment time is 2~4 h.

7. The method for preparing an antibacterial and dust-removal membrane of claim 1, wherein the temperature of said drier in Step (5) is 60~90° C.; the flow rate of nitrogen is 0.4~0.5 m/s, and the pressure is 0.5~0.6 MPa.

* * * * *